US00PP23384P2

(12) United States Plant Patent
Dunn

(10) Patent No.: US PP23,384 P2
(45) Date of Patent: Feb. 12, 2013

(54) ***PRUNUS INCISA* NAMED FPMSPL**

(50) Latin Name: *Prunus incisa*
Varietal Denomination: FPMSPL

(75) Inventor: Nick Dunn, Tenbury Wells (GB)

(73) Assignee: Carlton Plants LLC, Dayton, OR (US)

( * ) Notice: Subject to any disclaimer, the term of this patent is extended or adjusted under 35 U.S.C. 154(b) by 0 days.

(21) Appl. No.: 13/136,957

(22) Filed: Aug. 16, 2011

(51) Int. Cl.
*A01H 5/00* (2006.01)

(52) U.S. Cl. ..... Plt./216

(58) Field of Classification Search ..... Plt./216
See application file for complete search history.

*Primary Examiner* — Annette Para

(74) *Attorney, Agent, or Firm* — Chernoff, Vilhauer, McClung & Stenzel, LLP

(57) ABSTRACT

A new cultivar of *Prunus incisa* named FPMSPL that is characterized by its weeping habit, its variegated white and yellow-green summer foliage color, its variegated green, red-purple, grey-orange, orange-red and red-purple fall foliage color and its lack of seeds and fruits.

11 Drawing Sheets

Figure 1:
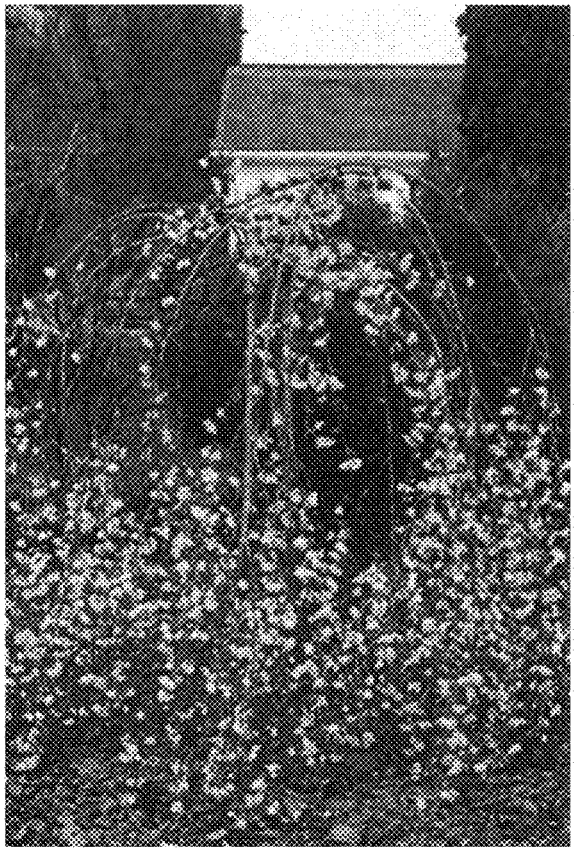

*Prunus incisa* named FPMSPL.

BACKGROUND OF THE INVENTION

The present invention relates to a new and distinct variety of *Prunus incisa*, which has been given the varietal name 'FPMSPL'. Nick Dunn discovered the new tree in a production field of *Prunus incisa* 'Snow Showers' as a chance branch sport growing in a cultivated area of a nursery in Tenbury Wells, Worcestershire, England. This cultivated area also contained other seedling and varietal *Prunus* trees. The new variety differed from these other seedlings and varieties of *Prunus* trees growing in this area by its variegated white and yellow-green summer foliage color and variegated green, red-purple, grey-orange (brown), orange-red and red-purple (pink) fall foliage color.

The parentage of this tree is unknown, but it is definitely a *Prunus incisa* type tree. Representative varieties within this species include 'February Pink', 'Kojo-no-mai', 'Mikinori', 'Oshidori Princess', 'Pendula', 'Praecox' and 'Snow Showers'.

The original tree was found as a single variegated branch sport from *Prunus incisa* 'Snow Showers' and at that time, grafting wood was collected and grafted on *Prunus avium*, then planted in a liner field. Having recognized this tree as unique, the inventor transplanted the new tree to a landscape setting adjacent to the nursery property in Tenbury Wells, Worcestershire, England in the spring of 2006, where it has remained since that time. It is now about 5 years old from a grafted liner. Plants of the new variety have been asexually reproduced in Tenbury Wells, Worcestershire, England. The characteristics of the new variety have been found to be strictly transmittable and the variety reliably reproduces true to form from one generation to another.

The description of this new *Prunus incisa* variety is based on observations of five-year old plants growing in Tenbury, Wells, Worcestershire, England.

SUMMARY OF THE INVENTION

As the original tree of the new variety was observed, the uniqueness of this tree became apparent because of its variegated white and yellow-green summer foliage color, and variegated green, red-purple, grey-orange (brown), orange-red and red-purple (pink) fall foliage color. These characteristics distinguish the new tree from other *Prunus* of which we are aware, such as *Prunus subhirtella* 'Pendula Rosea' (not patented), *Prunus incisa* 'Pendula' (not patented) and *Prunus incisa* 'Snow Showers' (not patented).

The new variety was asexually propagated by cleft grafting in 2006 at the direction of the inventor. The progeny have thus far proven to retain the unique weeping growth habit, variegated white and yellow-green summer foliage color, and variegated green, red-purple, grey-orange (brown), orange-red and red-purple (pink) fall foliage color of the original tree, with the variegation becoming more pronounced on vigorous extension growth and appearing later in the spring on leaves from older branches developing from the center of the leaves. This propagation and observation of the resulting progeny have proven the characteristics of the new variety to be firmly fixed and to reproduce true to type. Furthermore, these observations have confirmed that the new variety represents a new and improved variety of *Prunus incisa*, Fuji flowering cherry tree.

This unique tree differs from the species in its unique weeping growth habit compared to a more upright and spreading growth habit exhibited by the species, variegated white and yellow-green summer foliage color compared to glossy green summer foliage color exhibited by the species, variegated green, red-purple, grey-orange (brown), orange-red and red-purple (pink) fall foliage color compared to orange-red fall foliage color exhibited by the species, and its lack of seeds and fruits compared to the red-purple-black, drupe-shaped fruits typical of the species. *Prunus incisa* has no known patented or trademarked varieties.

The closest *Prunus incisa* variety similar in growth habit only is *Prunus incisa* 'Snow Showers'.

This unique tree differs from 'Snow Showers' by its white tinged with pink flower color rather than pure white flower color exhibited by 'Snow Showers', its variegated white and yellow-green summer foliage color compared to glossy green summer foliage color exhibited by 'Snow Showers', variegated green, red-purple, grey-orange (brown), orange-red and red-purple (pink) fall foliage color compared to orange-red fall foliage color exhibited by 'Snow Showers', and its lack of seeds and fruits compared to the red-purple-black, drupe-shaped fruits typical of those found on 'Snow Showers'.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

The accompanying photographic exhibits depict the shape of the tree, color of the foliage, bark, lenticels, glands, flowers and other characteristics of the new variety as nearly true as is reasonably possible to make the same in a color illustration of this character.

Figure 2:
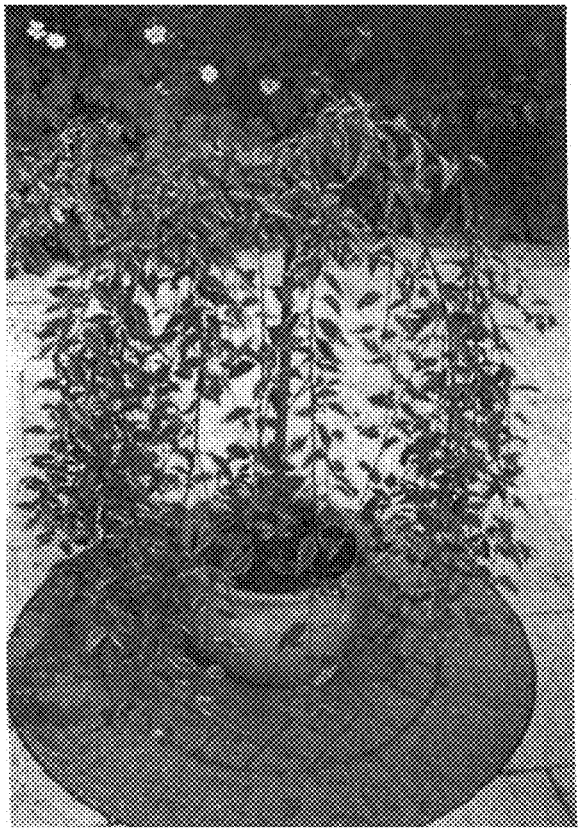
Figure 3:
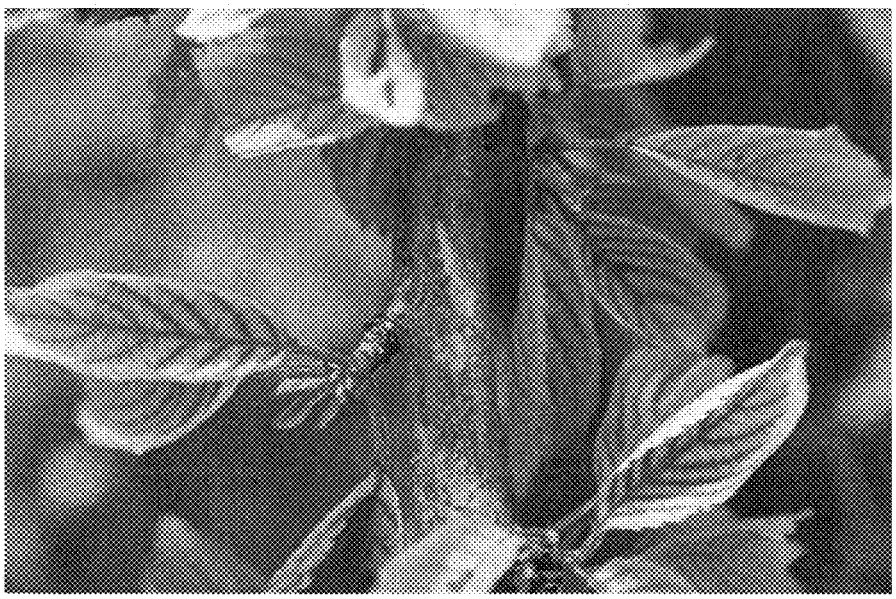
Figure 4:
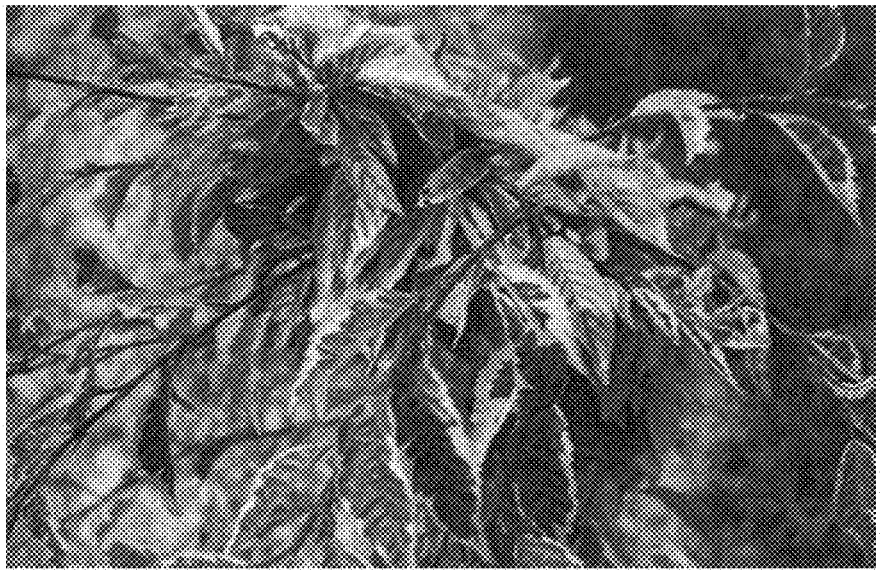
Figure 5:
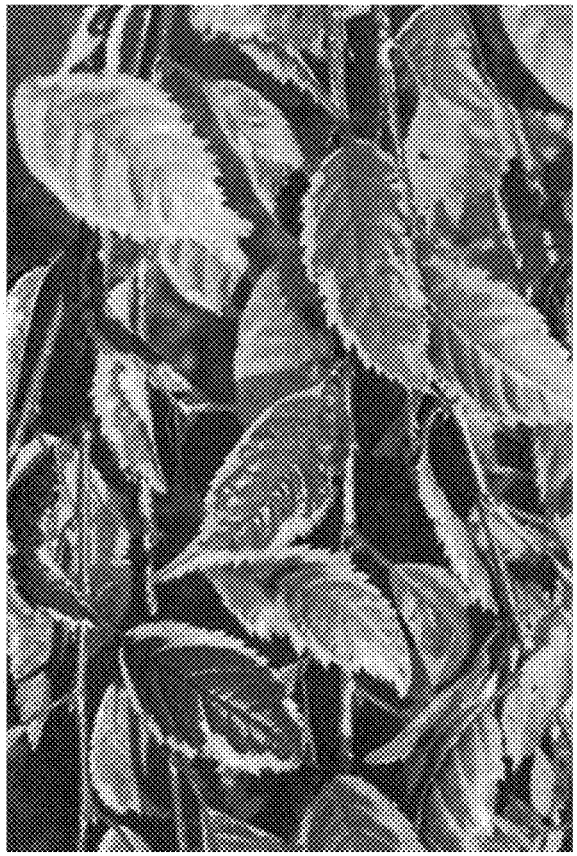

Photographic exhibits include the following:

FIG. 1—Photo of the tree without foliage showing unique weeping growth habit/form FIG. 2—Photo of the tree with leaves showing foliage density FIG. 3—Photo of variegated new foliage FIG. 4—Photo of variegated summer foliage color on mature plant FIG. 5—Photo of Variegated fall foliage color on mature plant (detail)

Figure 6:
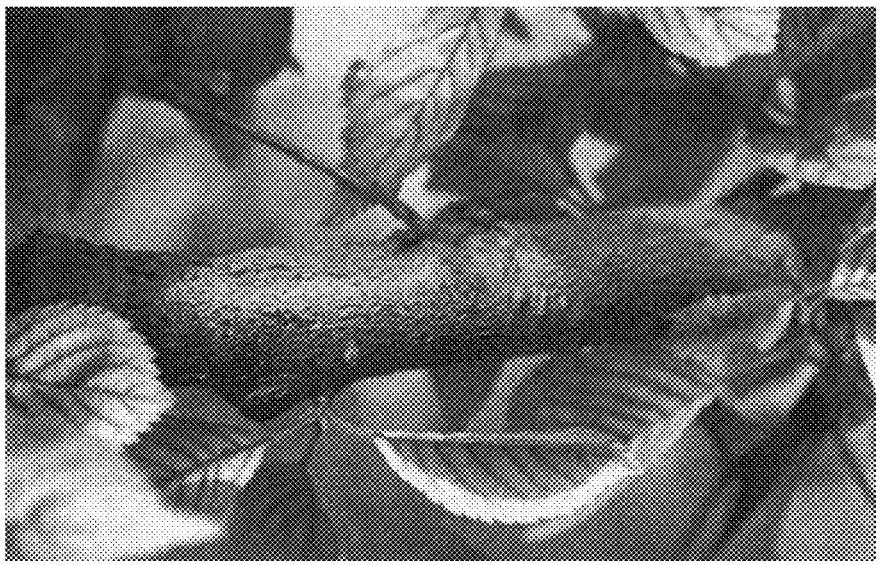

FIG. 6—Photo of the trunk bark

Figure 7:
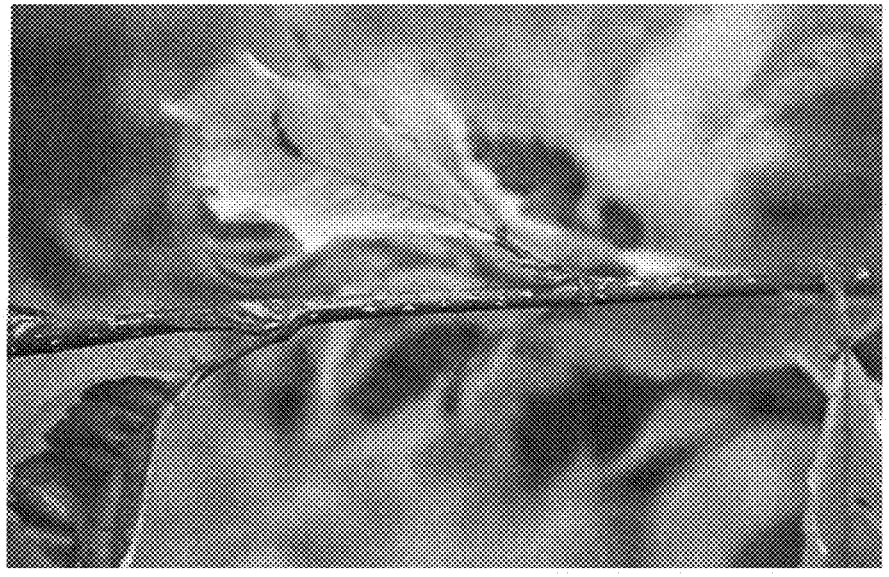

FIG. 7—Photo of stem/petiole

Figure 8:
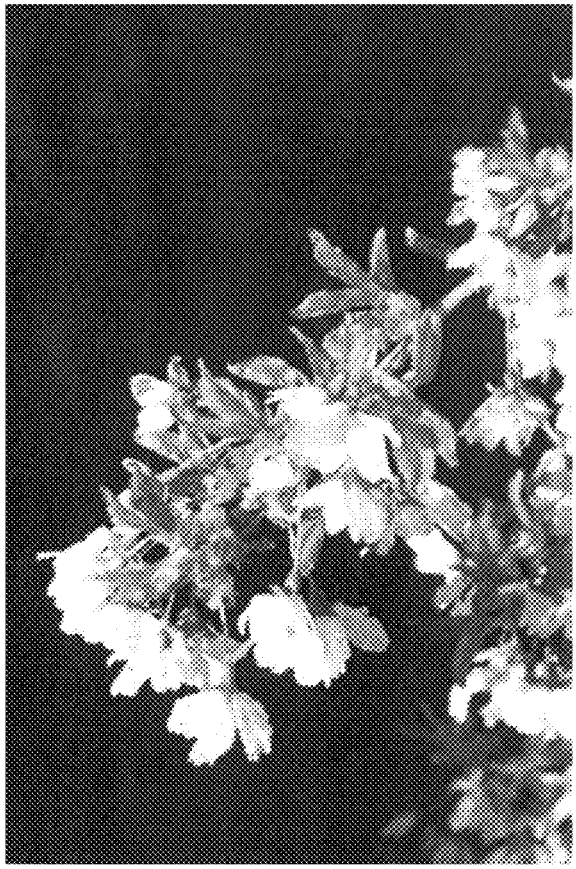

FIG. 8—Photo of flowers

Figure 9:
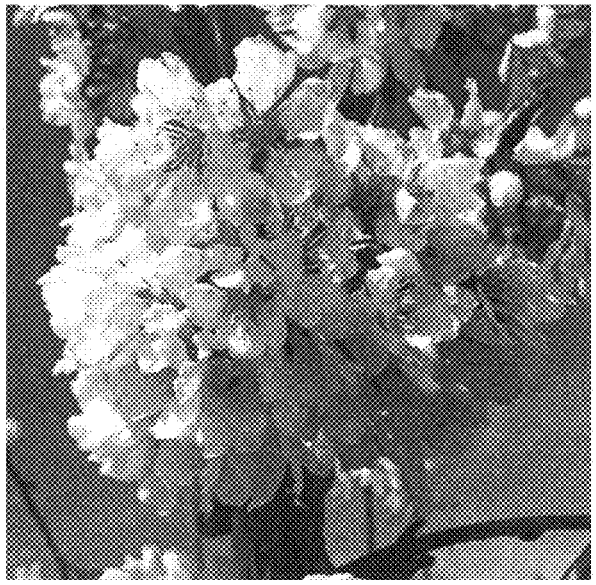

FIG. 9—Photo of flowers

Figure 10:
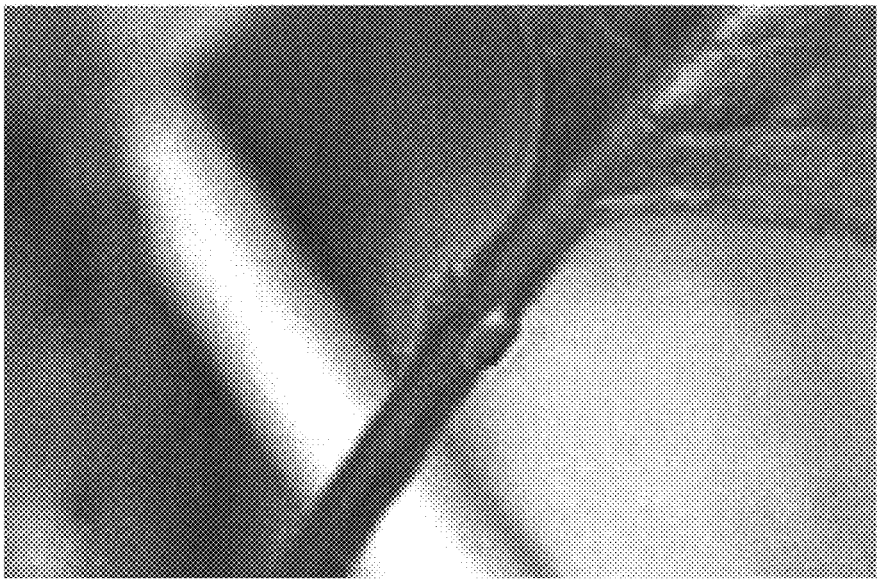

FIG. 10—Photo showing glands

Figure 11:
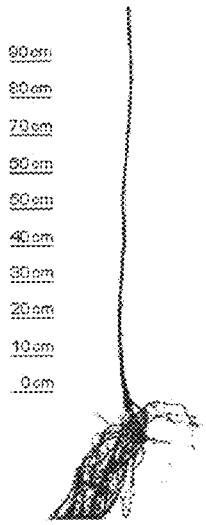

FIG. 11—Photo of root system (Prunus avium used for grafting)

DETAILED DESCRIPTION OF PREFERRED EMBODIMENTS

The original 'FPMSPL' variety of Fuji cherry tree is currently growing at an observation site in Tenbury Wells, Worcestershire, England. It is located in an area of the landscape that has a deep, alluvial soil type and receives approximately 30 inches of rain per year. Tenbury Wells, Worcestershire, England is in a zone comparable to USDA Hardiness Zones 6A-8B.

The new tree has not been observed under all growing conditions, and thus, variations may occur.

The following is a detailed description of the new variety of Fuji cherry tree with color terminology in accordance with The Royal Horticulture Society (R.H.S.) Colour Chart, © 2001, published by The Royal Horticulture Society in London. The observations are of the original five-year old tree growing in the landscape setting in Tenbury, Wells, Worcestershire, England, and of new progeny which have been recently virus certified and were propagated and growing at Carlton Plants, LLC at 14301 SE Wallace Road in Dayton, Yamhill County, Oreg., USA.

Parentage: Discovered as a chance branch sport growing in a cultivated area of a nursery in Tenbury Wells, Worcestershire, England. The parentage of this tree is believed to be by chimera with no pollen parent and no seed parent. Potential for reversion is low.

Tree shape: Weeping canopy, with no central leader (FIGS. 1 and 2).

Trunk: The trunk is typical of the species with a smooth appearance. At about age 2 years, the initially discovered tree had a diameter of about 0.5 inches in diameter measured 6 inches above the ground.

Bark: Bark (FIG. 6) is smooth and light grey-green in color (RHS Fan 4 — 198D).

Trunk lenticels:

*Shape.*—Oblong-elongated.

*Size.*—0.12 inches.

*Abundance.*—4-5 per inch.

*Color.*—Grey-orange (RHS Fan 4 — 165D).

Leaf stomata:

*Shape.*—Irregular.

*Size.*—0.02 inches.

*Color.*—Green (RHS Fan 3 — 132C).

Size and growth rate: Growth rate is slow. The original tree is currently 2 inches in diameter measured at 6 inches above the ground, it is 5 feet high, and 4 feet wide, thus providing an overall height to width ratio of about 1.25:1. Since transplanting to the observation site as a 0.5 inch caliper transplant, the original tree had an average growth in caliper of about 0.25 inches per year and vegetative growth of approximately 36 inches per year over 5 years.

Branching habit: Branching is strongly weeping with stiff branch attachments. Primary branches are smooth and slender emerging from the trunk at a 60-degree angle becoming a 90-degree angle parallel to the trunk at 10 inches (FIGS. 1 and 2).

Branches: Surface texture is smooth. Color is grey (RHS Fan 4 — 198D). Branch lenticels, on a branch having a 0.25 inch caliper, the average lenticels size is 0.15 inches. Shape is oval-elongated. Color is yellow-green (RHS Fan 3 — 154D) to grey-yellow (RHS Fan 4 — 160 D).

Foliage: The tree has leaves that are shaped similar to those of the species. Shape: opposite, simple, ovate to obovate, sharply serrulata, 2 to 3 inches long, 1 to 1.5 inches wide, with 0.15 inch pointed lobes. Sinuses are terminal, 1 to 1.5 inches long and smooth. Mature summer foliage color of upper surface is variegated green and yellow-green and is glossy (RHS Fan 3 — 141A green and RHS Fan 3 — 154 B yellow-green) (FIG. 4); mature summer foliage color of lower surface is variegated green and yellow-green and is glossy (RHS Fan 3 — 141A green and RHS Fan 3 — 154 B yellow-green). Mature fall foliage color of upper surface is variegated green, red-purple, grey-orange (brown), orange-red and red-purple (pink) and is glossy (RHS Fan 3 — 141A green, RHS Fan 2 59B red-purple, RHS Fan 4 174A grey-orange, RHS Fan 1 N34A orange-red and RHS Fan 2 64B red-purple) (FIG. 5); mature fall foliage color of lower surface is variegated green, red-purple, grey-orange (brown), orange-red and red-purple (pink) and is glossy (RHS Fan 3 — 141A green, RHS Fan 2 59B red-purple, RHS Fan 4 174A grey-orange, RHS Fan 1 N34A orange-red and RHS Fan 2 64B red-purple) (FIG. 5).

Immature spring foliage color of upper surface is light yellow-green, slightly mottled in appearance and is glossy (RHS Fan 3 145C yellow-green) (FIG. 3); immature spring foliage color of lower surface is yellow-green, slightly mottled in appearance and is glossy (RHS Fan 3 145C). Vein color is green and is predominant on immature spring foliage (RHS Fan 3 131C). Pubescence: location, lower surface on new foliage; color light green (RHS Fan 3 142C). Overall shape — serrulate. Base: cuneate. Apex: truncate. Surface texture: smooth and glossy.

Petiole: Average length approximately 1 inch to 1.5 inches.

*Diameter.*—0.25 inches (FIG. 7). Surface texture is smooth and glossy.

*Color.*—Grey-red on immature petioles (RHS Fan 4 178B).

Glands: Predominant, 1-2 per leaf and orange-red in color (RHS Fan 1 N34A) (FIG. 10).

Buds: Typical of the species, being rounded.

*Size.*—0.15 inches to 0.25 inches long.

*Diameter.*—0.25 inches.

*Color.*—Grey-brown (RHS Fan 4 N199C) to grey-brown (RHS Fan 4 200 D), with ciliate scale margins. Buds are formed prior to leaf emergence and are retained before flowering for 5-7 days.

Flowers: Typical of the species are Monoecious with no fragrance. The staminate catkins are pendent and clustered. The individual flowers are white with a pink tinge (RHS Fan 4 155D) and are comprised of a 5-lobed red-purple calyx (RHS fan 2 63A) that encloses 2 to 3 red-purple (pink) stamens (RHS Fan 2 69B). Pistillate flowers are: solitary or on 2 to 3 pendulous spikes from the petioles prior to emergence of the new leaves. Individual pistillate flowers (FIGS. 8 and 9) consist of: an oval-shaped, notched (0.2 inches deep) or lobed calyx surrounding the ovary, with the whole partly enclosed in an involucres. Flowers are 0.5 inches deep and 0.5 inches wide, which is 10-15% larger than the species or the closest known variety, *Prunus incisa* 'Snow Showers'. Flowers develop on buds opening April $10^{th}$-$20^{th}$ with full bloom April $20^{th}$-$30^{th}$, approximately 5 days later than the species or the closest known variety, *Prunus incisa* 'Snow Showers' with similar bloom longevity lasting 5-10 days.

Fruit: Non-existent, which is atypical of the species and of the closest known variety, *Prunus incisa* 'Snow Showers'.

Root system: The root system is typical of the species being fibrous with a strong tap root development if on their own root or typical of *Prunus avium* (FIG. 11) or whatever similar understock may be used if grafted.

Pest and disease resistance: Typical of the species — generally healthy and trouble free. Tolerance to pH has been observed between 5.0-7.0 millivolts. Tolerance to other various soil conditions is unknown.

Winter hardiness: Observed to be typical of the species — USDA Zones 6A-8B.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A new and distinct cultivar of *Prunus incisa* named FPMSPL, as shown and described herein.

* * * * *